United States Patent
Cordani et al.

(10) Patent No.: US 6,440,160 B1
(45) Date of Patent: Aug. 27, 2002

(54) EMERGENCY STRETCHER KIT

(75) Inventors: Peter J. Cordani, Palm Beach Gardens; Lawrence J. Dutton, Port St. Lucie; Ken Rickert, Boynton Beach; Bruce Gritter, Big Pine Key; William A. Cordani, Palm Beach Gardens, all of FL (US)

(73) Assignee: Dyn-O-Spine, Inc., Riviera Beach, FL (US)

( * ) Notice: Subject to any disclaimer, the term of this patent is extended or adjusted under 35 U.S.C. 154(b) by 31 days.

(21) Appl. No.: 09/709,808

(22) Filed: Nov. 9, 2000

(51) Int. Cl.$^7$ .................................................. A61F 7/00
(52) U.S. Cl. ............................. 607/114; 607/96; 5/625; 128/870; 62/4
(58) Field of Search ................... 607/114, 96; 5/625, 5/626; 128/845, 870, DIG. 15; 62/4

(56) References Cited

U.S. PATENT DOCUMENTS

| | | | | |
|---|---|---|---|---|
| 3,986,505 A | * | 10/1976 | Power ..................... 128/132 R |
| 5,433,741 A | * | 7/1995 | Truglio ...................... 607/104 |
| 5,603,729 A | * | 2/1997 | Brown et al. ................ 607/114 |
| 5,699,568 A | * | 12/1997 | Couldridge .................... 5/628 |
| 5,749,374 A | * | 5/1998 | Schneider, Sr. ............. 128/870 |
| 5,755,756 A | * | 5/1998 | Freedman, Jr. et al. ...... 607/110 |

* cited by examiner

Primary Examiner—Denise L. Esquivel
Assistant Examiner—Marc Norman
(74) Attorney, Agent, or Firm—McHale & Slavin

(57) ABSTRACT

An emergency stretcher kit is used in the treatment of certain bone and joint injuries. The kit includes a mat formed with an absorbent layer and an impermeable layer. A pocket attached to the absorbent layer contains a dual compartment packet having a thermal composition inside. The seal between the compartments is broken and the thermal composition is mixed to create an endothermic reaction to cool the pocket. The mat has Velcro straps and contact adhesive patches to secure the mat on a backboard and about the patient.

17 Claims, 3 Drawing Sheets

EMERGENCY STRETCHER KIT

FIELD OF THE INVENTION

This invention relates to the field of emergency medical care. The emergency stretcher kit may be used in initial treatment of a patient or First Aid to stabilize and transport an injured person. The device is useful in alleviating the effects of shock and, also, swelling that accompany bone and joint injuries. The device is especially helpful when used with a stretcher or backboard in situations where head and spinal injury is present or suspected.

BACKGROUND OF THE INVENTION

When an unexpected injury occurs, there are several immediate actions recommended, including preventing shock, stabilizing the injured part of the body to prevent further injury, and transporting the patient to a medical facility. In addition, applying a cold compress will reduce swelling while awaiting proper diagnosis and treatment. Also, in situations in which the patient is bleeding, it is necessary to attempt to stop the bleeding and to contain the spilled blood for sanitary disposal.

Usually, each of the aforementioned functions is accomplished with a different instrument or apparatus. What is needed in the emergency trauma art is an integrated system which can be quickly and easily deployed and applied to the patient to simultaneously provide certain necessary treatments.

DESCRIPTION OF THE PRIOR ART

There are many types of First Aid kits designed for many different possibilities of injury. Most kits include a carrying case and several bandages and implements for use on the injured member.

There are some thermal blankets with connections and internal tubing for circulating a thermal fluid, either hot or cold, such as disclosed in U.S. Pat. Nos. 5,072,875 and 6,086,609. The thermal fluid is applied to the appropriate part of a body by blanket or bandage.

Also known in the prior art, as shown in U.S. Pat. No. 5,150,707, are thermal packs having gel forming polymers inside. These packs may be heated or frozen before use and conveniently disposed of after use.

What is lacking in the prior art is a system that does not require extraneous apparatus to produce a thermal packet for application to an injured body member.

Also, there is a need for a system for use with spinal and head injuries to reduce swelling that may be used in conjunction with a conventional backboard that stabilizes the spine during movement. It has been found that a reduction in the core body temperature decreases multiple pathophysiological events occurring to the spinal cord and brain as a result of such injuries, including acute brain trauma and spinal cord injury.

Further, there is a need for a blanket or covering for the patient that absorbs and holds large amounts of liquids without becoming saturated or leaking.

SUMMARY OF THE INVENTION

An emergency stretcher kit for use in the treatment of certain bone and joint injuries. The kit includes a mat formed with an absorbent layer and an impermeable layer. A pocket attached to the absorbent layer contains a dual compartment packet having a thermal composition inside. The seal between the compartments is broken and the thermal composition is mixed to create an endothermic reaction to cool the pocket. The mat has Velcro straps and contact adhesive patches to secure the mat on a backboard and about the patient.

Accordingly, it is an objective of the instant invention to teach the use of a emergency stretcher kit that includes a mat for applying about an injured patient to adjust body heat provide protection from the elements.

It is a further objective of the instant invention to teach the use of a two component thermal packet in conjunction with the mat to prevent swelling of the injured member. The thermal packet is stored at ambient temperature but become cold when the two elements are mixed within the packet. The thermal packet may reduce the core temperature of the body by up to 10 degrees.

It is yet another objective of the instant invention to teach the use of a supplemental cover mat to completely encase the patient.

It is a still further objective of the invention teach the use of the mat with other devices for stabilizing a patient, such as a backboard or stretcher.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
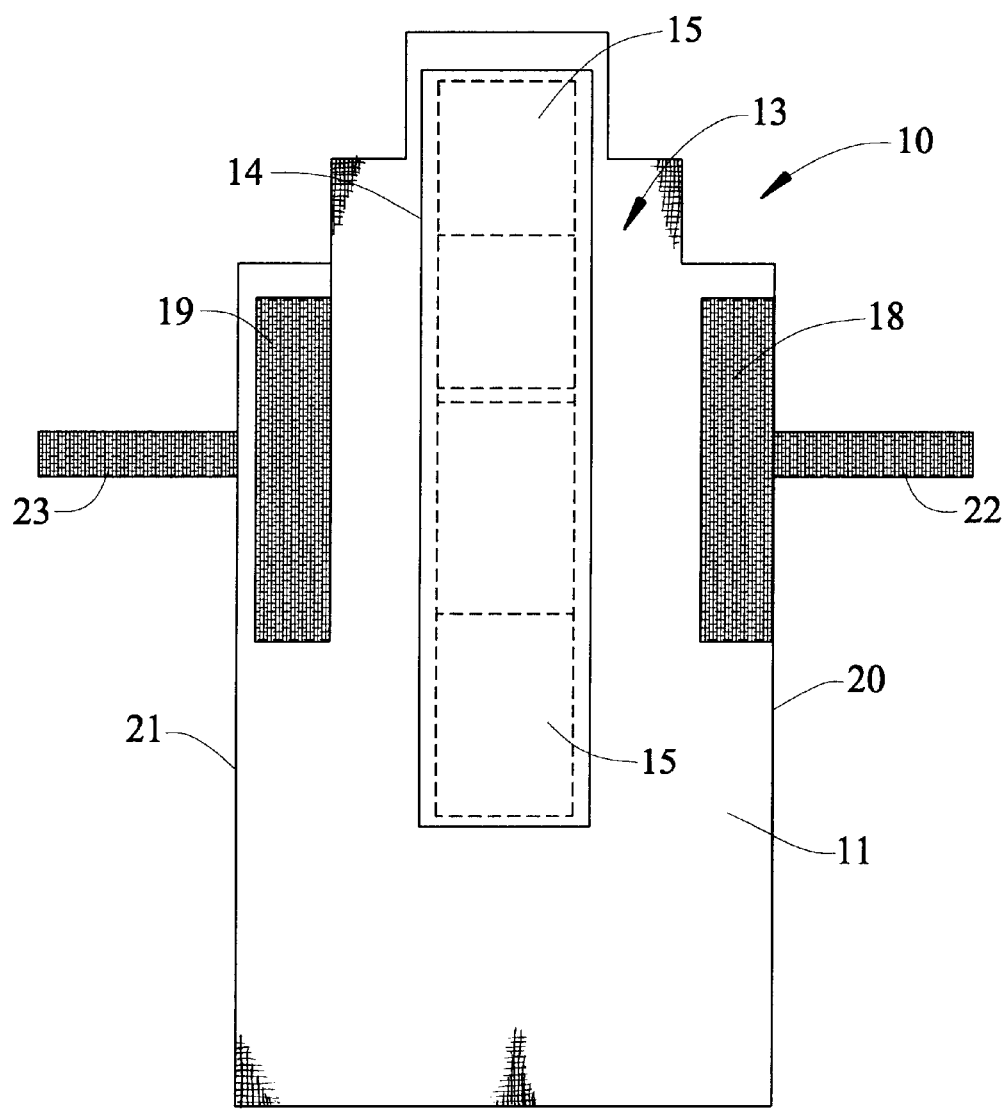
FIG. 1 shows a plan view of the absorbent surface of the mat.

The emergency stretcher kit has a mat 10 that may be made in various sizes and shapes to accommodate different patients. In the preferred embodiment shown in FIG. 1, the mat 10 is of a general shape to conform with a supine person. The major length of the mat approximates the height of an average person and the minor width approximates the width of the shoulders and the thickness of the body. The mat 10 is made of a layer 11 of non-woven polypropylene fibers continuously bonded to an impermeable layer 12 of polyester or polyethylene film. The layers may be bonded together by heat sensitive adhesive. The fibrous layer is absorbent and retains liquids well because of the interstices between fibers. Because of the absorbency of the mat, any hazardous materials, including blood, are retained in the mat until proper disposal. This construction also allows for adjusting and maintaining the patient's body heat.

The central area 13 is designed to be located adjacent the neck and spine of a patient. An elongated pocket 14 is centrally formed on the absorbent layer of the central area. It extends along the major length of the mat a distance approximating the length of the spine. The periphery of the pocket may be heat sealed to the absorbent layer or otherwise attached by adhesives. In the preferred embodiment, the pocket contains a dual compartment thermal packet 15. However, one edge of the pocket may remain unattached for access to the interior space. This unattached edge may have cooperating fasteners, such as Velcro, snaps or buttons, for temporarily closing the pocket. The pocket 14 is made of a mesh material which houses a thermal packet or packets.

Figure 4:
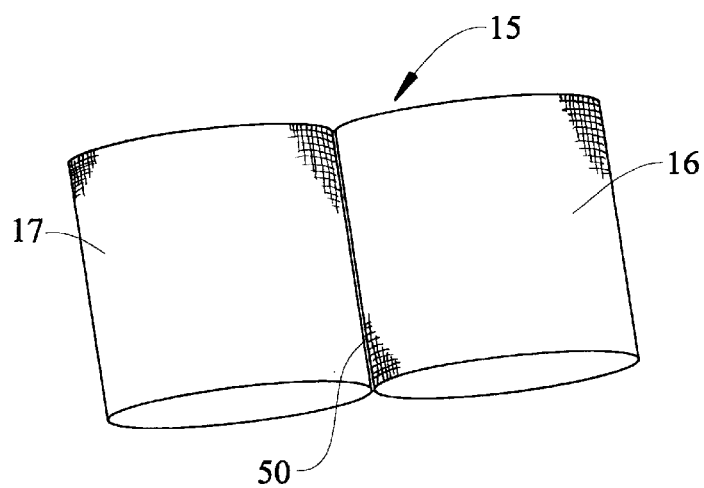
FIG. 4 shows a perspective of a dual compartment packet.

The thermal packet 15, shown in FIG. 4, is made of a sealed impervious polymer material. An interior heat seal 50 is formed in the packet creating dual compartments. One compartment 16 has a food grade hydrocarbon gelling agent. The other compartment 17 has a composition, such as a mixture of ammonium nitrate and magnesium nitrate, that when mixed with the gelling agent forms an endothermic reaction to reduce the temperature of the composition. The reaction reduces an ambient temperature packet to near freezing condition. The packet 15 or a plurality of packets, as shown in FIG. 1, may be sealed in the pocket 14 or the packets may be carried separately from the mat until ready for use.

In another embodiment of the mat, secondary pockets 18 and 19 may be located near the periphery of the mat. These pockets approximate the location of the person's arms when the mat is in use and are designed to carry dual compartment thermal packets 15. These pockets are constructed in accordance with the structure of the pocket 14.

The opposite longitudinal edges, 20 and 21, of the mat 10 each have a cooperating strap of Velcro, 22 and 23, extending outwardly therefrom. These straps are used to secure the margins of the mat about the sides of a patient to maintain body heat and for transportation.

Figure 2:
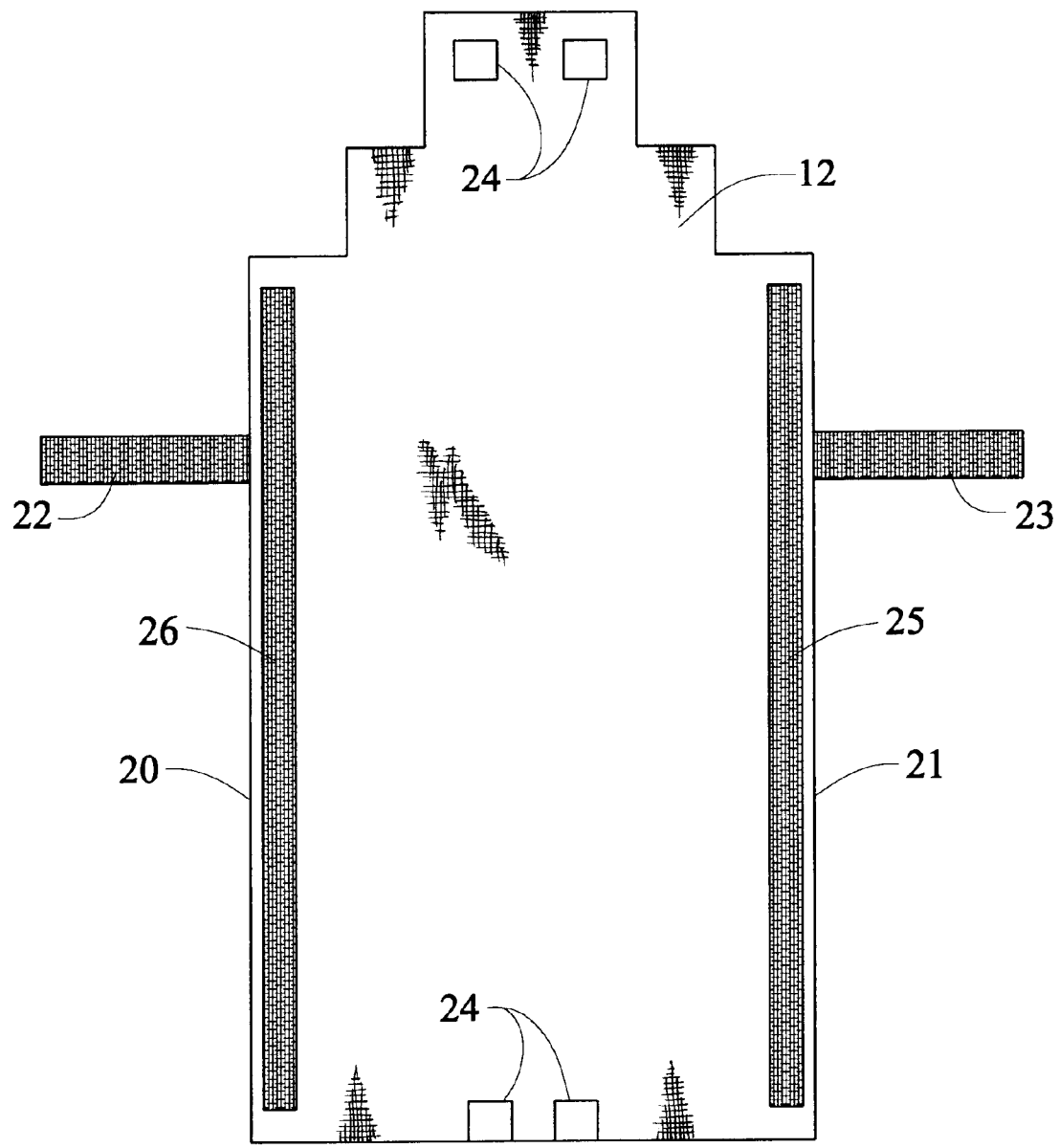
FIG. 2 shows a plan view of the impermeable surface of the mat.

The embodiment shown in FIG. 2 may be used with a backboard or other device used to immobilize a patient's neck and back. The impermeable layer 12 has a plurality of attached adhesive patches 24. The contact adhesive of these patches is exposed by removing a peel-away protective strip. The patches are then adhered to a backboard, stretcher, or other device to fix the position of the mat on the backboard. In this manner, the mat may be used to reduce swelling is spinal and head injury cases while the patient is immobilized for transport. The thermal packs will reduce the core of the body preferably in the range of 2 to 6 degrees.

Figure 3:
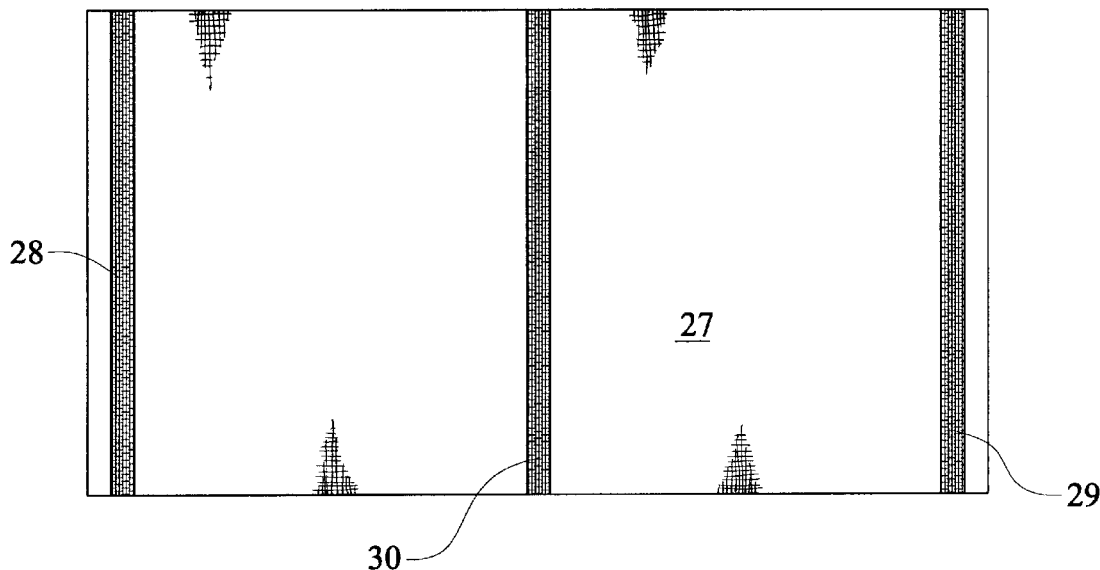
FIG. 3 show a plan view of the impermeable surface of the cover mat.

The impermeable layer 12 also has attached to the longitudinal edges elongated panels of Velcro fasteners 25 and 26. These strips are used to secure the cover mat 27, shown in FIG. 3.

The cover mat 27 is of similar dimensions as the mat 10 and is made of the same material. The cover mat has strips 28, 29 and 30, of Velcro fasteners extending across the minor width of the cover mat. These strips cooperated with the fasteners 25 and 26 to temporarily adhere the cover mat to the mat.

In operation, the emergency stretcher kit would be carried in a carrying bag or the entire kit could be enfolded within the mat. The kit may be carried in emergency vehicles or by individuals. When the kit is deployed for use with an injured patient having a suspected spinal injury, the operator would peel off the cover strips from the contact adhesive patches 24 and adhere the mat to a backboard. The operator would then rupture the heat seal 50 in the packet and knead the packet until the elements are well mixed and the temperature is reduced. The backboard and mat are then placed under the patient so that the spine is immobilized and in contact with the cold pocket. The Velcro straps 22 and 23 are then secured to secure the mat about the patient. Depending on weather conditions or the condition of the patient, the cover mat may be used to cover the patient and the Velcro strips 25, 26, 28, 29 and 30 are used to secure the cover mat to the mat.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A disposable emergency stretcher kit comprising
   a) a thin flexible mat adapted to cover a stretcher or backboard, said mat having a major length and a minor width, said mat formed of two layers, one layer being an impermeable backing material and the other layer being an absorbent material, an elongated pocket is formed on said absorbent material along the major length of said mat, said elongated pocket located approximately on the center line of said major length, said pocket adapted to contain a dual compartment packet, and
   b) a plurality of said dual compartment packets having a breakable seal between said compartments, each of the compartments of said dual compartment packet containing a reaction element of a thermal composition, whereby when said breakable seal is breeched said elements mix and create an endothermic reaction.

2. An emergency stretcher kit of claim 1 wherein said mat comprises cooperating straps of Velcro material extending outwardly from the edges of the major length of said mat, said straps adapted for releasable connection with each other forming said mat into a channel shaped configuration with an axis along said major length.

3. An emergency stretcher kit of claim 2 wherein said mat comprises a releasable fastening on said impermeable material for securing said mat to a stretcher or backboard, said releasable fastening composed of adhesive patches affixed to said impermeable material, said adhesive patches having a peel-away protective strip.

4. An emergency stretcher kit of claim 1 wherein said mat comprises Velcro strips mounted on said impermeable material along the major length.

5. An emergency stretcher kit of claim 4 comprising c) a cover mat adapted to be placed over a patient, said cover mat of approximate size of said mat, said cover mat having an absorbent surface and an impermeable surface, said Velcro strips cooperating with said cover mat to releasably connect said cover mat and said mat.

6. An emergency stretcher kit of claim 5 wherein said cover mat comprises a plurality of Velcro strips on said impermeable material of said cover mat, said Velcro strips extending along the minor width of said cover mat.

7. An emergency stretcher kit of claim 5 comprising d) a carrying bag containing said mat, said cover mat and said plurality of packets.

8. An emergency stretcher kit of claim 1 wherein said mat comprises a second and a third elongated pocket formed on said absorbent material, said second elongated pocket located along one margin of the major length of said absorbent material and said third elongated pocket located along the second margin of the major length of said absorbent material, said second and third elongated pockets adapted to contain dual compartment packets.

9. An emergency stretcher kit of claim 1 wherein said elongated pocket is formed of a thin mesh material affixed to said mat about the periphery, said elongated pocket having an opening thereinto for inserting said packets.

10. An emergency stretcher kit of claim 1 wherein a first element of said thermal composition contained in one compartment of said dual compartment packet comprises ammonium nitrate and the second element of said thermal composition contained in the second compartment of said dual compartment packet comprises a gelling agent whereby when said first and second elements are mixed an endothermic reaction creates a cold stable gel.

11. An emergency stretcher kit for securement about an injured patient to prevent shock and reduce swelling comprising a thin flexible mat having a periphery with a major length and a minor width, said mat formed of an outer impermeable layer and a coextensive inner absorbent layer, an elongated centrally located pocket attached to said absorbent material and extending from said periphery along said major length, a dual compartment packet containing an endothermic composition contained in said elongated pocket, and cooperating Velcro straps attached at one end to said mat and extending from said periphery along said major length for confining the injured patient.

12. An emergency stretcher kit of claim 11 wherein said mat includes Velcro strips attached to said impermeable surface along said major length of said periphery.

13. An emergency stretcher kit of claim 12 wherein said kit includes a cover mat having an absorbent surface and an impermeable surface, said cover mat having the general shape and dimensions of said mat, said cover mat having Velcro strips attached to said impermeable surface and extending in direction of said minor width, said Velcro strips adapted to cooperate with said Velcro strips of said mat.

14. An emergency stretcher kit of claim 11 wherein said mat includes a second and a third pocket along said periphery of said major length, said second and third pocket each containing a dual compartment packet with said endothermic composition therein.

15. An emergency stretcher kit of claim 11 wherein said mat has a plurality of adhesive fasteners on said impermeable surface, said adhesive fasteners covered by peel-off strips.

16. A method of treating an injured patient comprising the steps of a) providing an elongated mat having an absorbent side and an impermeable side, said mat having an elongated pocket attached to said absorbent side, said pocket containing a dual compartment packet, said dual compartments separated by a breakable partition, each of said compartments containing an element of an endothermic composition which when mixed form a cold stable gel, Velcro straps having one end attached to each side of said elongated mat and extending outwardly therefrom, b) placing said mat on a smooth surface,
  c) applying pressure to said pocket and said packet within to rupture said breakable partition,
  d) kneading said pocket and said packet until a cold stable gel has formed,
  e) placing said injured patient on said mat so that said cold gel contacts the injury,
  f) bringing said Velcro straps together about said patient to secure said mat about said patient.

17. A method of claim 16 wherein said smooth surface is a backboard and said mat has adhesive fasteners on said impermeable surface including the step of adhering said mat to said backboard.

\* \* \* \* \*